United States Patent [19]

Comte et al.

[11] Patent Number: 4,875,475
[45] Date of Patent: Oct. 24, 1989

[54] DEVICE FOR TREATING A BONE

[75] Inventors: Pierre-André Comte, Pully; Hans Schürch, Titterten, both of Switzerland; Gebhard Ritter, Mainz-Finthen, Fed. Rep. of Germany

[73] Assignee: Synthes (U.S.A.), Paoli, Pa.

[21] Appl. No.: 803,953

[22] Filed: Dec. 2, 1985

[30] Foreign Application Priority Data

Nov. 30, 1984 [CH] Switzerland .................. 5720/84

[51] Int. Cl.$^4$ .............................................. A61F 5/04
[52] U.S. Cl. ............................................... 128/924 Y
[58] Field of Search ........... 128/924 Z, 924 E, 924 Y, 128/128; 623/16, 18

[56] References Cited

U.S. PATENT DOCUMENTS

| 1,584,780 | 5/1926 | Langworthy | 128/924 E |
| 4,498,468 | 2/1985 | Hansson | 128/924 K |

FOREIGN PATENT DOCUMENTS

| 0118778 | 9/1984 | European Pat. Off. | 128/924 Y |
| 0145666 | 12/1984 | European Pat. Off. | |
| 2246274 | 3/1974 | Fed. Rep. of Germany | 128/924 Z |
| 0619132 | 9/1980 | Switzerland | 128/924 Z |
| 1593440 | 6/1977 | United Kingdom | |

OTHER PUBLICATIONS

Manual der Osterosynthese.
FIGS. 1, 2, 3 of U.S. Pat. No. 3,334,624.
Synthes "Original ASIF Instruments and Implants" pp. 63 & 64.

Primary Examiner—Richard J. Apley
Assistant Examiner—David J. Isabella
Attorney, Agent, or Firm—Davis Hoxie Faithfull & Hapgood

[57] ABSTRACT

The device comprises an intramedullar nail adapted to be driven into a hollow bone. The proximal terminal nail segment comprises an internal thread and a transversely penetrating longitudinal slot adapted to receive a screw to penetrate through the nail and to be screw-connected with the bone. The distal terminal nail segment comprises two transversely throughgoing holes each adapted to receive a screw to be screw-connected with the bone. An adjusting means comprises a bolt as adjusting member provided with an external thread screwed directly into the internal thread of the nail, or screwed into the internal thread of an insert in turn screwed into the internal thread of the nail, the bolt being adapted to be brought into direct or indirect engagement with the screw transversely penetrating through the longitudinal slot. By turning the bolt the screw may be pressed toward the distal end of the nail and displaced toward the same. The adjusting means or member may be inserted into the nail in rapid and simple manner after the nail has been driven into the hollow bone, and may be brought into a position, in which it engages the screw that transversely penetrates through the longitudinal slot. The entire adjusting means is adapted to remain inside the nail, until such time as the nail is removed from the hollow bone.

2 Claims, 3 Drawing Sheets

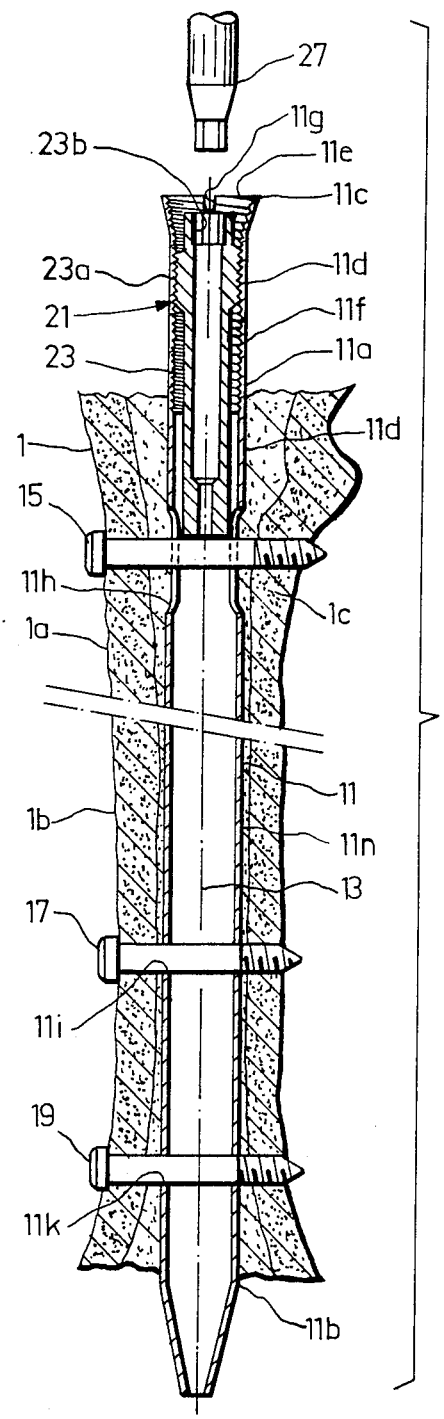
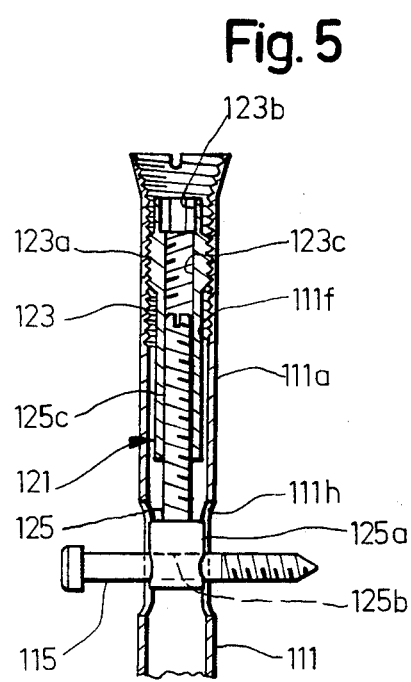
Fig. 5
Fig. 4
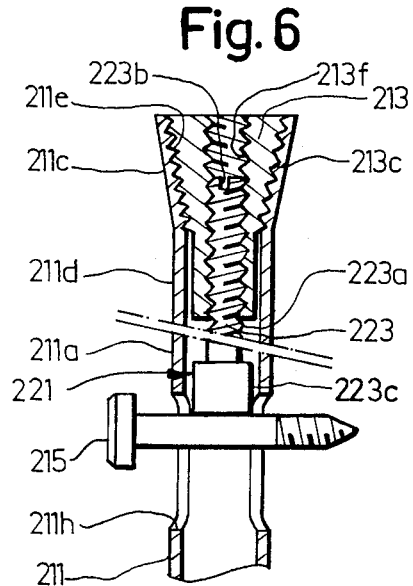
Fig. 6

DEVICE FOR TREATING A BONE

The present invention refers to a device for treating a bone and comprising an intramedullary nail for use in bone surgery. The nail to be placed into the bone comprises at its one end a first terminal nail segment having a longitudinal slot guiding a screw transversely penetrating through it, and at its other end a second terminal nail segment provided with at least one hole to receive a screw to penetrate transversely through the nail. The nail preferably provided with an axial through hole, is made hollow at least in the region of its first terminal segment and means are provided to generate a force to act between aligned bone pieces. An elongated adjusting means is generally provided to be brought into engagement with the screw guided within the longitudinal slot of the first terminal nail segment. This adjusting means is arranged for adjusting the force to act between aligned bone pieces. Such devices are used in surgical practice for holding together broken or intentionally severed pieces of a bone during an operation and for connecting them to assure their properly growing back together again.

When using the device, the nail is driven from the proximal end of the bone into the intramedullary space or cavity thereof. The first terminal nail segment is arranged to be located in the proximal region, whereas the second terminal nail segment in the distal region of the bone. The first terminal nail segment shall therefore be referred to as proximal terminal nail segment, the second terminal nail segment as distal terminal nail segment. After the nail has been driven into the bone, the proximal terminal nail segment and the distal terminal nail segment are connected with screws with the corresponding terminal bone segments, to interlock the bone with the nail.

The German Patent Disclosure Publication (Offenlegungsschrift) No. 22 46 274 discloses a device comprising a nail and a compression bolt adapted to be inserted into the proximal terminal segment of the nail. A locking piece comprising a throughgoing longitudinal opening is loosenably fastened to the proximal end of the nail by means of a bayonet lock. The compression bolt comprises a shaft penetrating through said longitudinal slot, the shaft being adapted to be fixedly locked in various sliding positions by means of a set screw screwed into the locking piece. The adjustment of a screw penetrating through the slot and screwed into a bone piece is accomplished by means of a separate adjusting device fastened temporarily onto the locking piece in a loosenable manner. This adjusting device comprises a housing and a threaded spindle adapted to engage the compression bolt by way of a compression spring. If the set screw screwed into the locking piece is loosened, it becomes possible, by turning the threaded spindle, to exert a compression force onto the compression bolt. This compression force is transmitted onto the screw penetrating through the slot, to thus displace the screw toward the distal end of the nail. When the screw penetrating through the slot has reached the desired position, the set screw is screwed tight and the adjusting device is removed.

This device has certain disadvantages. Thus, after the nail has been driven into the bone during a surgical operation, and the set screw set in place, several additional steps are required: to get the locking piece fastened to the nail, to get the adjusting device fastened to the locking piece, to tighten the set screw after having adjusted the compressing bolt, and lastly to separate the adjusting device from the locking piece. The set screw must by necessity be external to the bone, to make it accessible for being locked tight. There is a danger involved in this, namely, that the set screw and the part of the locking piece which holds the set screw and protrudes from the medullar space of the bone may injure the patient's soft tissues, when the patient moves. An additional danger results from the fact, that since the compression bolt is held in place only by the set screw that engages the smooth cylindrical outer surface of the bolt shaft, the compression bolt may become displaced after the adjusting device has been removed, and could fail to fulfill its function. Furthermore, the fact that the compression bolt is not directly fastened to the nail itself, and that in order to form a bayonet lock the nail must be provided with a notch which weakens it, will negatively influence the stability of the connection. Lastly, this device known in the art fails to provide for the possibility of exerting a pulling force unto the screw that penetrates through the slot, to have the effect of pulling the screw away from the distal end of the nail, a step which may be desirable in certain special cases.

It is an object of the invention to create a surgical device for treating a bone, which device avoids the mentioned disadvantages of the aforementioned known device and similar devices known in the art.

A further object of the invention is to create a surgical device which provides a stable and reliable connection with the bone pieces.

A further object of the invention is to create a surgical device which is simple in design and flexible in its use and possesses no inherent dangers of injuring the patient.

A further object of the invention is to create a surgical device which may be inserted into and withdrawn from the bone simply and rapidly, and which comprises subtle possibilities for the adjustment of the desired force or force per unit area pressure between the fractured bone pieces.

A further object of the invention is to create a surgical device in which its adjusting means may be left entirely within the device for longer periods.

A further object of the invention is to create a surgical device by which compression alone, or compression and tension may be exerted onto the bone pieces to be connected.

A further object of the invention is to create a surgical device in which the adjusting means may be displaced within a increased range of distances, to make the device useful for a wider variety of bone lengths than has been hitherto possible.

A further object of the invention is to create a surgical device, in which a tool and possible a torque wrench may be used for rotating the adjusting member, to accurately set the force or force per unit area to act between the aligned bone pieces.

SUMMARY OF THE INVENTION

The foregoing and other objects are attained in accordance with one aspect of the invention through the provision of the following features:

A nail to be placed into the bone comprises a first terminal nail segment provided with a longitudinal slot for guiding retaining member such as a screw penetrating through it, and a second terminal segment, that faces away from said first terminal nail segment and is connected with said first terminal nail segment indisplaceably in the longitudinal direction of the nail. Said second terminal nail segment comprises at least one hole adapted to receive a screw to penetrate therethrough, whereby the nail is made hollow at least in the region of its first terminal segment. Adjusting means are provided and adapted to be brought into engagement with the screw that penetrates through said slot and to apply to said screw a force directed in the longitudinal direction of the nail. According to the invention, the adjusting means is adapted to be accommodated radially within the inner boundaries of the intramedullary nail and comprise an adjusting member adapted to be displaced within the nail in axial direction by rotation, to set and adjust said force and to be left therein after adjustment.

Various other features which characterize the invention and specific embodiments thereof are claimed in the claims annexed and forming part of the specification.

The invention will be more fully appreciated from its following detailed description when considered in connection with the accompanying drawings.

DESCRIPTION OF THE DRAWINGS

In the drawings:

FIG. 4 shows a longitudinal section through parts of the device, at about the same scale as FIG. 3, FIG. 5 shows a longitudinal section through a part of another embodiment of the device, FIG. 6 shows a longitudinal section through a part of a further embodiment of the device.

DETAILED DESCRIPTION OF THE PREFERRED EMBODIMENTS

Figure 1:
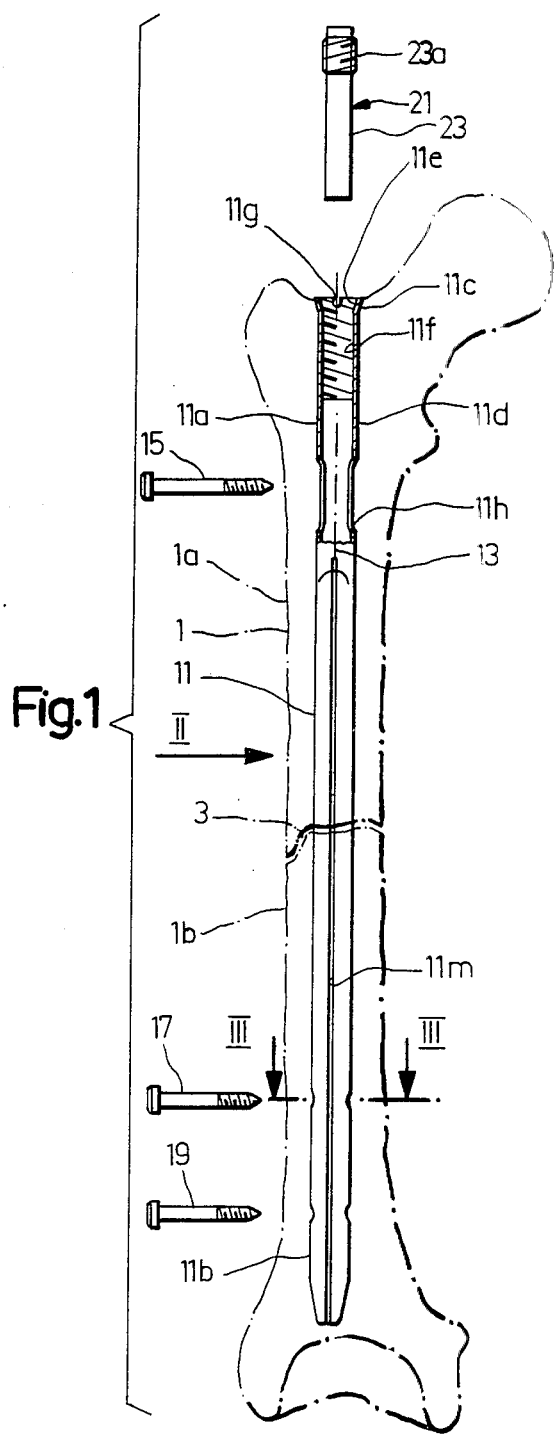
FIG. 1 shows an exploded illustration of a device for treating a hollow bone.

The device illustrated in FIG. 1 is intended for treating the bone 1 of a human being or perhaps of an animal; it may be used specifically for treating the hollow bone of one of the extremities, for example the femur, the outline of which is shown in FIG. 1 by dash-dotted lines, the bone being fractured at the location 3 into at least two bone pieces 1a, 1b.

Figure 3:
FIG. 3 shows at a larger scale a cross-section through the nail, taken along the line III—III in FIG. 1.
Figure 2:
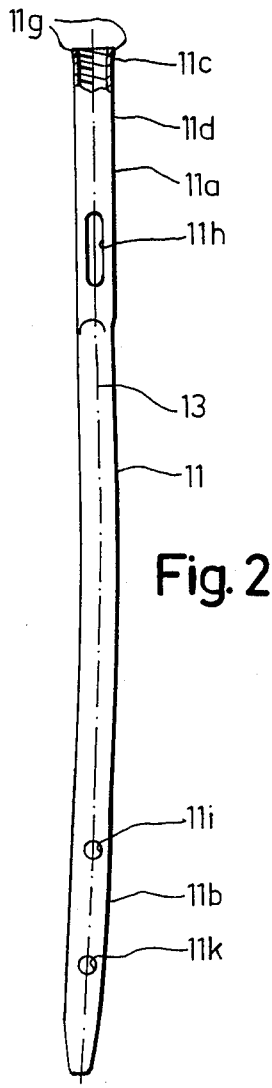
FIG. 2 shows a view of the nail, looked at in the direction indicated by the arrow II in FIG. 1.

The device comprises as its main component a so-called medullar or intramedullar nail consisting of a one-piece metallic nail 11 shown in FIGS. 2 and 3, and comprising a throughgoing longitudinal hole open at both free ends of the nail 11. The nail 11 may have its longitudinal axis 13 run slightly curved, or straight, as the case may be, along its longitudinal plane of symmetry. The nail 11 comprises at its ends the two terminal segments 11a, 11b facing away from each other. When the nail 11 is inserted into the medullar space, i.e. into the bored out medullar cavity of the hollow bone 1, the one, first, proximal terminal nail segment 11a will be located at the proximal end of the bone 1, the other, second, distal terminal nail segment 11b being located at the distal end of the bone 1.

The proximal terminal nail segment 11a is straight or at most very slightly curved, and its wall displays essentially rotational symmetry with respect to the longitudinal axis 13. The proximal terminal segment 11a comprises at its free end a partial segment 11c tapering from this free end in the direction of the other nail end essentially conically. Adjoined thereto is a partial segment 11d essentially cylindrical in shape. The conical partial segment 11c and the adjoining outer portion of the cylindrical partial segment 11d are provided with conical and cylindrical internal threads 11e and 11f, respectively. The two internal threads 11e and 11f are designed to have the same sense of rotation or winding, as well as the same pitch, and are arranged to smoothly go over into each other at the inner end of the conical internal thread 11e. The conical partial segment 11c is provided with two grooves 11g starting at the free end of the segment and being arranged to diametrically oppose each other.

Near its end facing toward the central nail segment, the proximal terminal segment 11a is provided with a longitudinal slot 11h that transversely penetrates through the nail and crosses the hollow space thereof. The distal terminal nail segment 11b is provided with two holes 11i and 11k that transversely penetrate through the segment 11b and are displaced relative to each other along the longitudinal axis 13, both holes 11i and 11k being realized as a through bore arranged to cross the hollow space of the nail. The arrangement is such, that the essentially plane longitudinal central surface of the longitudinal slot 11h, in which surface will come to lie the axis of the screw 15 that transversely penetrates through the longitudinal slot 11h and the axes of the holes 11i, 11k, runs perpendicular to the longitudinal plane of symmetry of the nail.

At a peripheral location within the aforementioned longitudinal surface or plane of symmetry, the wall of the hollow nail 11 is provided with a narrow longitudinal slot 11m, which extends from the free end of the distal terminal nail segment 11b, along the same, and along the central nail segment 11n, up into the adjoining end of the cylindrical proximal terminal nail segment 11a. The central and longest nail segment 11n and the distal terminal segment 11b possesses cross-sectional contours in the shape of a rounded triangle, for example convexly curved throughout, and having essentially the shape of a tri-rondular solid of constant diameter, as shown in FIG. 3. At the same time the distal terminal nail segment 11b is arranged to taper away from the partial segment containing the holes 11i, 11k, in the direction of its free end.

The device also includes a screw 15 destined to be inserted into the slot 11h, furthermore, two screws 17 and 19 destined to be inserted into the holes 11i and 11k, respectively, and an elongated adjusting means 21, which consists solely of an adjusting and engaging member, namely a one-piece metallic bolt 23. The length of the adjusting means 21 constituted by the bolt 23 is made preferably smaller than the distance measured from the center of the longitudinal slot 11h to the free end of the proximal terminal segment 11a, and is for example approximately or at least equal to the distance measured from the free end of the proximal terminal segment 11a to the end of the longitudinal slot 11h located nearer this free end. Near its one end the bolt 23 comprises a segment provided with a cylindrical external thread 23a, which, as shown in FIG. 4, is adapted to be screwed into the cylindrical internal thread 11f of the nail 11.

The remaining segments of the bolt 23 possess each a smooth cylindrical outer surface having a diameter somewhat smaller than the diameter of the external thread 23a and smaller than the internal diameter of the terminal nail segment 11a. At the same time the radial play of the threadless segments of the bolt 23 within the hollow space of the terminal nail segment 11a is so dimensioned, that the bolt 23 is axially adjustable in a manner yet to be described in more detail, even if the proximal terminal nail segment 11a were slightly curved in the longitudinal section. In order to render an adequate axial adjustment of the bolt 23 possible even if the first terminal segment 11a were slightly curved, the external thread 23a of the bolt is made relatively short as compared to the entire length of the means 21. The length of the external thread 23a is arranged to be not more than 40% and preferably not more than 30%, or for example not more than or approximately 20% of the entire length of the adjusting means 21 and thus of the length of the bolt 23 too. Furthermore, the length of the external thread 23a is not more than approximately 1.5 times the outer diameter of the external thread 23a, and is for example approximately or at most equal to the outer diameter. For the rest, the internal threads 11e, 11f and the external thread 23a are preferably carried out as fine threads.

The bolt 23 is provided with a polygonal hole 23b, such as a hexagonal hole, at its end facing away—in its assembled state—from the nail 11 and located nearer the external thread 23a, so that a rotation and torque transmitting tool 27 such as a wrench comprising a hexagonal stud may temporarily be brought into a rotation transmitting engagement with the bolt 23. At its other end the bolt 23 is provided with a smooth radial end surface. Also, the bolt 23 may comprise a throughgoing longitudinal hole.

If the device is to be used for treating the bone 1, then, in the course of a surgical operation the bone pieces 1a, 1b will be aligned relative to each other and the medullar cavity bored into as deeply as necessary. Then, a handle and a drive-in tool will temporarily be fastened onto the conical partial nail segment 11c and the nail 11 will be driven into the medullar space or cavity starting out from the proximal end of the bone, so that the nail 11 will reach the position shown in FIGS. 1 and 4. Then the position of the holes 11i, 11k will be determined by using an X-ray device and a sighting device, and screw holes aligned with the holes 11i, 11k will be drilled into the bone 1 and provided with threads. The screws 17 and 19 may now be inserted into the holes 11i, 11k and screwed into the bone 1, or more accurately, into the bone piece 1b, so that they will penetrate through the holes 11i, 11k with only slight radial play and connect the bone piece 1b with the nail 11 in an essentially non-displaceable manner. Then, by using the sighting device, a screw hole will be drilled into the bone piece 1a and made to align with a portion of the longitudinal slot 11h, by preference with a portion located near the proximal end of the longitudinal slot 11h. Then, a thread will be cut into this screw hole too, and the screw 15 will be screw-connected through the longitudinal slot 11 with the bone piece 11a. In this way, the threads within the threaded holes cut into the bone will be located, on the one side of the nail 11, at least in part within the corticalis portion 1c of the bone which has comparatively high density.

At this point, the bolt 23 that constitutes the adjusting and engaging member and also the adjusting means 21 will be inserted into the hollow space of the proximal terminal nail segment 11a, the tool 27 will be brought into engagement with the bolt 23 and the latter will be screwed-in to a depth at which its radial end surface which faces toward the central segment of the nail 11 will come into engagement with the cylindrical stud of the screw 15. Screwing now the bolt 23 deeper into the nail will cause a displacement of the screw 15 with respect to the nail 11 within the longitudinal slot 11 which laterally guides the screw 15 with only slight play, this displacement taking place in the direction of the nail 11 and toward the distal terminal segment 11b thereof. In the course of this displacement the screw 15 will take the bone piece 1a along. The bolt 23 will now be screwed-in further, until the bone piece reaches its desired position and the two bone pieces 1a, 1b will get pressed against each other at the place of fracture 3 with the intended compression force. As soon as the bone piece 1a occupies this position in relation to the nail 11, it will be possible to again separate the tool 27 from the bolt 23. The bolt 23 will now assume a position, in which it will be contained at least approximately but preferably completely within the hollow space of the nail 11. The bone pieces 1a, 1b will now be connected with the nail 11 by means of the screws 15, 17, 19, i.e., they will be interlocked therewith.

After the operation the nail 11, the screws 15, 17, 19, and the adjusting means 21 will remain in the bone 1, until the bone pieces will be grown together again at the place of fracture 3. The upper bone piece 1a can now be subjected—while the patient stands or walks—to the weight of his body parts supported by said bone piece 1a. The force thus developed will press the bone piece 1a against the bone piece 1b, thus adding to the force generated by the adjusting means 21, with the result, that the bone piece 1a will now be able to move closer to the bone piece 1b, while the screw 15 moves away from the bolt 23. The adjusting means 21 will thus make possible a dynamic compression of the bone pieces, with the result, that even though the bone piece 1a is able to move in the longitudinal direction of the nail 11, it is not able to move any further away from the screws 17, 19 screwed into the distal bone segment, than the limit position shown in FIG. 4 and determined by the setting of the adjusting means 21. At the same time the longitudinal slot 11h that guides the screw 15 will make sure, that the bone piece 1a will not rotate around the longitudinal axis 13 in the course of its displacement.

The embodiment of the device, part of which is shown in FIG. 5, includes a hollow nail 111 built identical or similar to the nail 11, and specifically comprises a first proximal terminal segment 111 a provided with a cylindrical internal thread 111f, and a longitudinal slot 111h. The device also includes a screw 115 corresponding to the screw 15, furthermore, screws not shown in the drawing but corresponding to the screws 17, 19, and an adjusting means 121 consisting of two metal bolts, a first bolt 123 and a second bolt 125. The first bolt 123 serves as adjusting member or adjusting bolt that is rotatable by a tool and axially displaceable by such a rotation. The second bolt 125 serves as engaging member or engaging bolt for engaging the screw 115 to be displaced. The first bolt 123 comprises an external thread 123a corresponding to the external thread 23a, a polygonal hole 123b corresponding to the polygonal hole 23b, and a longitudinal bore extending from the polygonal hole 123b to the other end of the bolt 123 and provided with an internal thread 123c. The second bolt 125 includes a cylindrical head 125a provided with a through hole 125b running perpendicular to the bolt axis and realized to a considerable part as a bore, furthermore, a thinner threaded part provided with an external thread 125c and comprising a screw slot or the like at its free end, said threaded part being screwed into the internal thread 123c of said first bolt 123.

The two bolts 123, 125 are thus interconnected for the transmission of tension and compression, while at the same time being displaceable relative to each other along their longitudinal axes and being rotatable around the same relative to each other. The external threads 123a and 125c of the two bolts 123 and 125 possess different winding directions and for example different pitches too. Thus, for example, the internal threads 111f of the nail and the external threads 123a of the bolt 123 screwed thereinto may be right-handed threads, whereas the internal thread 123c of the bolt 123 and the external thread 125c of the bolt 125 screwed thereinto may be left-handed threads.

When using the device illustrated in FIG. 5 the nail 111 is driven into the medullar space of the hollow bone to be treated, then the screws corresponding to the screws 17 and 19 and the adjusting means 121 and the screw 115 are set in place, so that the shaft of the screw 115 are set in place, so that the shaft of the screw 115 is guided within the through hole 125b with only slight display. By now rotating the first bolt 123 in relation to the nail 111, by means of a tool corresponding to the tool 27, the screw 115 will be guided within the longitudinal slot 111h non-rotatably with respect to the longitudinal axis of the nail 11, and will in turn prevent any rotation or the second bolt 125 with respect to the nail. If, for example, the second bolt 125 is arranged to have the head-sided terminal segment of its threaded part protrude from the first bolt 123, and the screw 115 is inserted into the bone in a way to have it at first occupy a position near the lower end of the longitudinal slot 111h, i.e., near the end facing toward the distal end of the nail, and if subsequently the first bolt 123 is rotated in the counterclockwise direction as looked at from the proximal end of the nail, then the bolt 123 will become displaced upwardly and away from the distal end of the nail and it will also pull the second bolt 125 upwardly and away from the distal end of the nail.

Since the threaded portion of the second bolt 125 is pulled during rotation of the first bolt 123 into the internal thread 123c of the latter, the second bolt 125 will become displaced from the distal end of the nail 111 by a larger distance than the first bolt 123. By rotating the first bolt 123 in the aforementioned sense of rotation it is possible to pull away the screw 115 and the bone segment screw-connected therewith from the bone segment screw-connected to the distal terminal nail segment. In this way it is possible to stretch the bone, which in certain cases may be useful. Evidently, the first bolt 123 may also be rotated for adjusting the screw 115 along its longitudinal guiding slot 111h, so as to displace the screw 115 toward the distal end of the nail. Thus, whereas the device shown in FIGS. 1 to 4 allows only for compressing the bone, the device shown in FIG. 5 allows for optionally compressing or tensioning the bone.

In the embodiment of the device shown in FIG. 6 the nail comprises a proximal terminal segment 211a including a conical partial segment 211c and a cylindrical partial segment 211d. The conical partial segment 211c is provided with a conical internal thread 211e, whereas, in contrast to the cylindrical partial segments of the previously described nails 11, 111, the cylindrical partial segment 211d possesses a smooth threadless internal surface throughout; however, in analogy to the nails 11, 111, it possesses a longitudinal slot 211h. The segments not shown in FIG. 6 of the nail 211 may be of the same design as those of the nail 11. A one-piece insert 213 comprises a conical segment provided with a conical external thread 213c loosenably screwed into the conical internal thread 211e, and by preference a cylindrical stud adjoining the narrower end of the conical segment, and a coaxial through hole, specifically a bore, provided with a cylindrical internal thread 213f. An adjusting means 221 comprises an elongate adjusting and engaging member consisting of a one-piece adjusting and engaging bolt 223 having a shaft provided with a cylindrical external thread 223a screwed into the internal thread 213f of the insert 213. At its end facing away from the nail 211 the threaded shaft of the bolt is provided with a slot 223b to be engaged by a tool for imparting rotation. At its other end the bolt 223 preferably comprises a head 223c, radially protruding beyond its threaded shaft.

When using the device shown in FIG. 6, the insert 213 with the bolt 223 screwed into it is first screwed into the nail 211, after the latter has been driven into the bone. By rotating it, the bolt 223 may be axially displaced, to make it exert pressure upon a screw 215 which penetrates through the longitudinal slot 211h and is screw-connected with one of the bone pieces, with the purpose of pushing it toward the distal end of the nail. In all of the positions, in which it engages the screw 215, the adjusting bolt 223, which consists of a one-piece body, is completely contained within the hollow inner space constituted by the hollow space or the longitudinal hole of the nail and the through hole of the insert 213. The device shown in FIG. 7 comprises a nail 311 hollow along its entire length and comprising a first, proximal terminal segment 311a which—together with a central segment and a second, distal terminal segment consists of a one-piece body, so that the two terminal segments are connected non-displaceably in the longitudinal direction of the nail. The first terminal segment 311a comprises at its free end a conical partial segment 311c and a cylindrical partial segment 311d. The conical partial segment 311c is provided with a conical internal thread 311e, specifically a trapezoidal thread. The cylindrical partial segment 311d comprise a longitudinal slot 311h and a hole 311r realized as a bore and having its axis run perpendicular to the longitudinal axis of the nail 311 and parallel to the longitudinal central plane of the longitudinal slot 311h. The second terminal nail segment not shown in FIG. 7 and the central nail segment may have a construction identical or similar to the nail 11, and are specifically provided with a slot corresponding to the slot 11m. This slot may be provided with a narrow extension not shown in FIG. 7 and realized in the shape of a cut or slit and arranged to extend through the first, proximal terminal segment 311a up to the free end of the same, so that the peripheral wall of the nail 311 is subdivided over its entire length. The slot extension, if provided, should be made to run in the first terminal segment 311a so that the peripheral wall sections of the nail 311 subdivided by it should be made to form a dovetail-shaped recess and a dovetail engaging the same. By executing the slot extension in this way, the wall sections subdivided by it may be hooked into each other in such a way, that the first terminal nail sector 311a will be secured against spreading up. The dovetail may be located between the longitudinal slot 311h and the free end of the first terminal segment 311a, whereby the slot extension is preferably arranged to run through between the two openings of the nail wall that constitute the longitudinal slot 311h without crossing the same. As regards the possibility of constructing such an extension of a slot corresponding to the slot 11m, reference is made to the European Patent Disclosure Publication (Offenlegungsschrift) No. 0 145 666 and to the corresponding U.S. Pat. No. 4,628,920.

An insert 313 loosenably inserted into the first terminal segment 311a of the nail 311 comprises a terminal segment 313a protruding from the conical partial segment 311c and provided with a polygonal, specifically hexagonal, perimeter, furthermore a conical segment provided with a conical external thread 313c realized as a trapazoidal thread and screw- connected with the conical internal thread 311e of the nail, and a cylindrical segment that extends to near the longitudinal slot 311h. The insert 313 comprises a throughgoing longitudinal opening. This opening comprises a terminal segment facing toward the longitudinal slot 311h and comprising a cylindrical internal thread 313f and an enlargement 313h extending from the internal thread 313f up to the end of the insert 313 that protrudes from the nail 311. The peripheral wall of the insert 313 is provided with at least one hole 313i, more specifically with three holes 313i distributed over its periphery, between the conical external thread 313c and the cylindrical internal thread 313f.

A screw 315 corresponding to the screw 15 penetrate through the longitudinal slot 311h. An adjusting means 321 disposed within the nail 311 comprises an adjusting and engaging member constituted by a metallic one-piece bolt 323. This bolt 323 comprises a cylindrical segment provided with an external thread 323a screwed into the internal thread 313f of the insert 313 and comprising at its end facing away from the longitudinal slot 311h a threadless terminal segment provided with a polygonal hole 323b, specifically a hexagonal blind hole. Disregarding this blind hole, the bolt 323 possesses a full cross-section and a constant diameter over its entire length, said diameter being at least or approximately equal to the diameter of the shaft of the screw 313 that penetrates through the longitudinal slot 311h.

Figure 7:
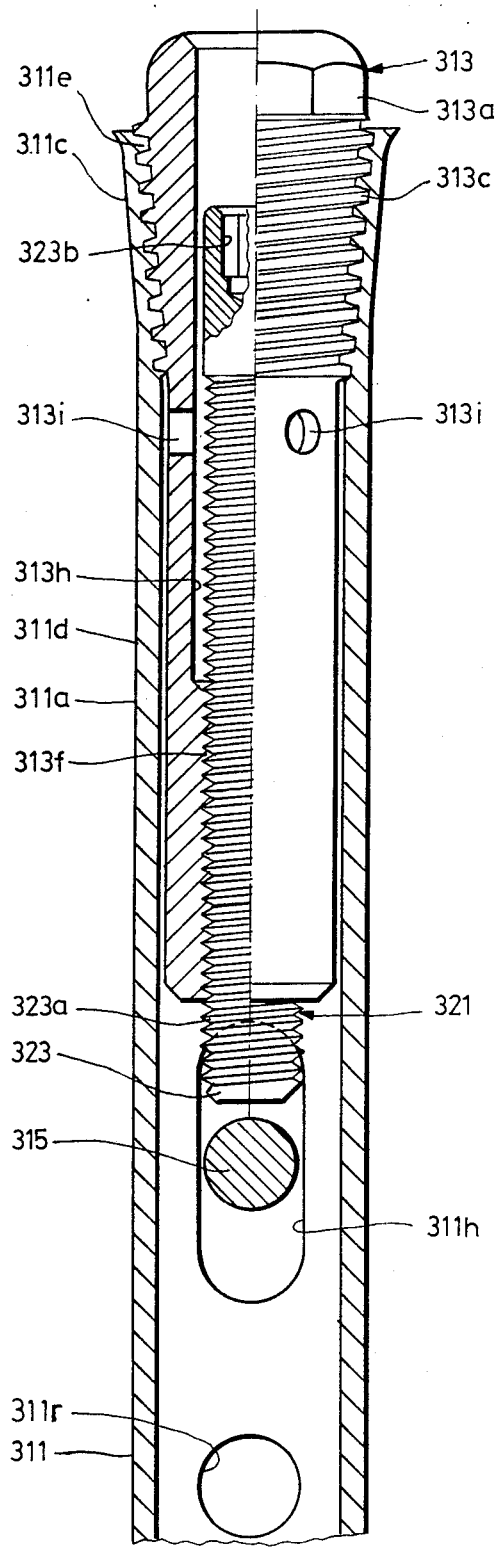
FIG. 7 shows a longitudinal section through a part of a further embodiment of the device.

When using the device shown in FIG. 7, the insert 313 and the bolt 323 are screwed into the nail 311 after the nail 311 has been driven into a bone. The bolt 323 may then be axially displaced by rotation, to engage the screw 315 and to push the same against the second, distal end of the nail 311. The polygonal terminal segment 313a and the polygonal hole 323b constitute an entrainment and torque transmitting means, which may be engaged on the insert 313 and the bolt 323, respectively, by suitably constructed tools, to effect rotation of the bolt 323 or insert 313. The bolt 323 is positioned in all its positions, in which it engages the screw 315 that penetrates through the longitudinal slot 311h and is displaceable along the same, completely within the inner space constituted by the hollow space of the nail 311 and the longitudinal opening of the insert 313.

Annular clearances are provided between the inner surface of the cylindrical partial nail segment 311d and the cylindrical segment of the insert 313, as well as between the inner surface of the insert 313 that bounds the enlargement 313h and the bolt 323. These two annular clearances constitute together with the holes 313i a passage arranged to connect the free inner space of the nail 311 with the surroundings of the first, proximal terminal nail segment 311a. This passage makes it possible, in analogy to the axial throughgoing hole of the bolt 23 of the device shown in the FIGS. 1 to 4, to carry away during the operation liquid secretions and/or gases from the hollow space of the nail, and for example to suck them off at the free nail end from the first terminal nail segment and/or to flush the hollow space of the nail.

When the adjusting means 321 has been adjusted by rotating the bolt 323 it may entirely remain inside the nail until the latter is removed from the hollow bone as it is also the case for the devices shown in the FIGS. 1 to 6.

If it is intended to use the nail 311 for applications requiring no compression of the bone pieces, the screw 315 may be screw-connected with the bone through the hole 311r realized as a bore, rather than through the longitudinal slot 311h. In this case, the nail 311 may be used without the bolt 323 and without the insert 313.

Thus, whereas in the device shown in FIGS. 1 to 5 the bolt 23 or 123, respectively, is axially adjustably screwed directly into an internal thread provided in the wall of a one-piece nail, the nail shown in the FIG. 6 and 7 consists in its mounted state so to speak of two parts, specifically, of the nail 211, 311 proper and hollow throughout and the insert 213, 313 loosenably screwed thereinto, the bolt 223, 323 being indirectly connected with the nail 211, 311 proper by way of said insert 213, 313.

It is self-understood, that the possibility exists for the nails 1, 111, 211 too, to provide the slot 11m or the slots corresponding to the slot 11m, as required, with an extension of the kind described in conjunction with the nail 311 and/or to provide in these nails holes corresponding to the hole 311r.

The bolts 125 and 223 shown in FIGS. 5 and 6 have full cross-sections. These devices, too, could be provided, however, with a passage to enable to carry away fluids from the hollow spaces of the nails 111 and 211 as it can be done for the nails 11, 311.

Evidently, the described devices may be used for treating not only broken hollow bones, but also hollow bones intentionally cut into pieces in the course of an osteotomic operation.

The devices described may be modified in other respects too. For example, the bolts 23, 123, 323 may be provided with entrainment and torque transmitting means different from the polygonal holes 23b, 123b, 323b such as with two diametrically opposed holes, or with a slot, or with cams protruding in axial direction, to enable a tool to temporarily come into a rotation transmitting engagement with the bolt. Conversely, the slot 223b of the bolt 223 may be replaced by a polygonal hole.

Furthermore, it may be possible to provide for example an adjusting means comprising two separate bolts to be used in a device for only compressing the bone. One of these bolts may then be constituted by the segments of the bolt 23, which comprise the external thread 23a and the polygonal hole 23b, and the other bolt by the remaining segment of the bolt 23, whereby the two bolts may be arranged to have their ends facing each other freely abut against each other. An embodiment of this kind could serve a useful purpose in cases, in which the proximal terminal segment of the nail or a partial region thereof is comparatively strongly curved or angled in relation to the remaining nail.

Furthermore, in a device for applying compression only to the bone, or in a device for optionally applying compression or tension, it may be possible to provide an adjusting means that comprises two bolts interconnected by connecting means, in a way to be rotatable around their common longitudinal axis or even to be swivelled around a point in space relative to each other, without being displaceable in the axial direction relative to each other.

The device shown in FIG. 5 could be modified in a way to have both internal threads 111f, 123c display similar winding directions; in this case, however, they would have to have different pitches and, evidently, the associated external threads 123a and 125c, respectively, would have to be made to correspond.

It would also be possible to use a single screw at the distal terminal segment of the nail, instead of the two screws 17, 19 shown in FIGS. 1 to 4.

The screws 15, 17, 115, 215, 315 could also be replaced by screws comprising each a cylindrical, smooth, i.e., threadless, part adjoining its tip, and a threaded part near its head-sided end for compensation.

Furthermore, the nail may be made to have, for example, a full cross-section in a certain region thereof; however, the nail should be made hollow at least in the region of its proximal terminal segment. Accordingly

What is claimed is:

1. Device for treating a bone having a fracture, said device comprising an elongated intramedullary nail having a longitudinal axis for insertion into the medulla of the bone across the bone fracture, said nail having a hollow first terminal segment at one end and a second terminal segment at the other end a longitudinal slot in the first terminal segment for receiving a retaining member extending generally transverse to the longitudinal axis, a hole in the second terminal segment for receiving a retaining member generally transverse to the longitudinal axis, and an adjusting member within said hollow first terminal segment for applying a force axially of the nail to a retaining member inserted in said slot in said first terminal segment, said first terminal segment having an internal thread and said adjusting member having an external thread to engage the internal thread of said first terminal segment, and a tool engaging means on said adjusting member for rotating said adjusting member to advance said adjusting member axially of the nail.

2. Device as claimed in claim 1, wherein said tool engaging means comprises a polygonal hole.

3. Device as claimed in claim 1, wherein said tool engaging means comprises a slot.

4. Device as claimed in claim 1, wherein said adjusting bolt consists of a one piece body.

5. The device claimed in claim 1 wherein the adjusting member is a bolt.

6. The device claimed in claim 1 wherein said first terminal segment at its end remote from said second segment has a conical portion flared outwardly from the longitudinal axis and wherein said internal thread is, at least in part, in said conical portion, said adjusting member consisting a conical insert having an external conical thread engaging the internal thread on said conical portion and an axial through hole with an internal cylindrical thread, and said adjusting means further comprising a bolt in said axial through hole, said bolt having an external thread engaging the internal thread of said through hole.

7. Device as claimed in claim 6, wherein said insert comprises means allowing a torque transmitting connection with a tool.

8. Device as claimed in claim 6 wherein the adjusting bolt is of a length such that it is contained completely within the nail when in contact with a retaining member inserted in the longitudinal slot.

9. The device as claimed in claim 6 and comprising an annular space between the outer surface of a portion of said insert and the inner wall of the nail, a second annular space between the outer surface of said adjusting bolt and the inner surface of the insert and a passage through the wall of the insert connecting said spaces.

10. Device as claimed in claim 1 wherein the length of the adjusting number is such that when advanced axially of the nail to a position in which it engages a retaining member in the longitudinal slot, it is inside the nail.

11. The device claimed in claim 1 wherein the two terminal nail segments are connected by a central segment, said central segment and the terminal segments constituting a one piece body.

12. The device claimed in claim 1 wherein said first terminal segment has a cylindrical portion and a central portion, the conical portion being at the end of said first terminal segment remote from the second terminal segment, said internal thread being in part in said conical portion and in part in said cylindrical portion, the pitch of the thread on said conical and cylindrical portions being the same.

13. The device claimed in claim 1 wherein said adjusting member comprises an insert having a threaded internal bore and an inner bolt having an external thread engaging the thread of the internal bore of said insert.

14. The device claimed in claim 1 wherein said adjusting member comprises an insert having external threads engaging the internal thread of said first terminal segment and an internally threaded internal bore, said adjusting member further comprising a bolt in said internal bore, said bolt having external threads engaging the internal thread of said bore and a head having a transverse aperture to receive a retaining member inserted in the longitudinal slot in said first terminal segment.

15. The device claimed in claim 14 wherein the external threads on said bolt have a band opposite to that of the external threads in said insert.

16. The device claimed in claim 15 wherein the external threads of said adjusting bolt and said inner bolt have different pitches.

17. Device as claimed in claim 1 wherein said intramedullar nail comprises a region of a generally triangular cross-section and having a perimeter convexly curved throughout.

18. Device as claimed in claim 17, wherein the perimeter of the nail in said region is realized as a constant diameter curve of tri-rondular configuration, said region being made to extend over a central nail segment and over the second terminal nail segment adapted to be accommodated inside the distal terminal segment of the bone.

19. Device as claimed in claim 1, wherein said first terminal nail segment comprises in addition to said slot a transverse bore for holding a screw undisplaceably in the elongated direction of the nail.

20. Device as claimed in claim 19, where said bore in the first terminal nail segment is arranged between the slot and the second terminal nail segment.

21. Device for treating a bone, the device comprising an axially elongated intramedullary nail to be placed into the bone, a first terminal nail segment comprising a longitudinal slot extending in the elongated direction and adapted to guide a first screw penetrating through it, and a second terminal nail segment, that faces away from said first terminal nail segment, and is connected with said first terminal nail segment indisplaceably in the elongated direction of the nail, said second terminal nail segment comprising at least one hole adapted to receive a second screw to penetrate therethrough, the nail is hollow at least in the elongated region of its first terminal segment, said two terminal segments and a central nail segment connecting them consist of a one-piece body, wherein at its free end the first terminal nail segment comprises a conical partial segment which tapers inwardly away from said free end and is provided with an internal conical thread receiving an insert provided with a conical external thread screwed thereinto, and wherein the insert is provided with an axial through hole comprising a cylindrical internal thread, and an adjusting member is provided having an external thread forming a screw connection with said cylindrical internal thread and adapted to be brought into engagement with the first screw that penetrates through said slot and to apply to the first screw a force directed in the elongated direction of the nail, the adjusting member further having engaging means adapted to be engaged by a tool for rotating the adjusting member so that the latter can be displaced within the nail in the axially elongated direction by rotation to set and adjust said force, and wherein said insert is adapted to be left in the nail and to hold the adjusting member after adjustment.

22. The device claimed in claim 21 wherein the adjusting member is of a length such that when it engages a retaining member in the longitudinal slot it is completely within the nail.

* * * * *

UNITED STATES PATENT AND TRADEMARK OFFICE
CERTIFICATE OF CORRECTION

PATENT NO. : 4,875,475
DATED : October 24, 1989
INVENTOR(S) : Pierre-Andre Comte, et al.

It is certified that error appears in the above-identified patent and that said Letters Patent is hereby corrected as shown below:

Claim 6, col. 11, line 62, "consisting" should be --comprising--.

Claim 12, col. 12, line 23, "central" should be --conical--.

Claim 12, col. 12, line 28, "on" should be --in--.

Claim 15, col. 12, line 44, "band" should be --hand--.

Signed and Sealed this

Thirtieth Day of October, 1990

Attest:

HARRY F. MANBECK, JR.

*Attesting Officer*     *Commissioner of Patents and Trademarks*